US011905335B2

United States Patent
Liao et al.

(10) Patent No.: US 11,905,335 B2
(45) Date of Patent: *Feb. 20, 2024

(54) PROTEIN-NANOPARTICLE CONJUGATE PURIFICATION METHODS

(71) Applicant: Bio-Rad Laboratories, Inc., Hercules, CA (US)

(72) Inventors: Jiali Liao, Hercules, CA (US); Tom Berkelman, Hercules, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 288 days.

This patent is subject to a terminal disclaimer.

(21) Appl. No.: 17/165,704

(22) Filed: Feb. 2, 2021

(65) Prior Publication Data

US 2021/0179736 A1 Jun. 17, 2021

Related U.S. Application Data

(63) Continuation of application No. 15/714,736, filed on Sep. 25, 2017, now Pat. No. 10,934,366.

(60) Provisional application No. 62/401,573, filed on Sep. 29, 2016.

(51) Int. Cl.
| | |
|---|---|
| *C07K 19/00* | (2006.01) |
| *A61K 47/69* | (2017.01) |
| *B01D 15/34* | (2006.01) |
| *B01D 15/38* | (2006.01) |
| *C07K 1/16* | (2006.01) |
| *C07K 16/00* | (2006.01) |

(52) U.S. Cl.
CPC .......... *C07K 19/00* (2013.01); *A61K 47/6929* (2017.08); *B01D 15/34* (2013.01); *B01D 15/3809* (2013.01); *B01D 15/3847* (2013.01); *C07K 1/16* (2013.01); *C07K 16/00* (2013.01)

(58) Field of Classification Search
None
See application file for complete search history.

(56) References Cited

U.S. PATENT DOCUMENTS

| | | | |
|---|---|---|---|
| 6,972,090 | B2 | 12/2005 | Boschetti et al. |
| 8,216,630 | B2 | 7/2012 | Autefage et al. |
| 8,382,987 | B2 | 2/2013 | Luchini et al. |
| 9,382,473 | B2 | 7/2016 | Chiu et al. |
| 9,383,299 | B2 | 7/2016 | Kunkel et al. |
| 10,814,305 | B2 * | 10/2020 | Liao ..................... B01J 20/3204 |
| 10,934,366 | B2 * | 3/2021 | Liao ....................... C07K 19/00 |
| 2003/0125529 | A1 | 7/2003 | Boschetti et al. |
| 2010/0204455 | A1 | 8/2010 | Gervais et al. |
| 2011/0045574 | A1 | 2/2011 | Bergstrom et al. |
| 2013/0034854 | A1 | 2/2013 | Ashworth-Sharpe et al. |
| 2013/0217866 | A1 | 8/2013 | Falkenstein et al. |
| 2013/0248451 | A1 | 9/2013 | Hall et al. |
| 2014/0193876 | A1 | 7/2014 | Goerke et al. |
| 2015/0377869 | A1 | 12/2015 | Berkelman et al. |

FOREIGN PATENT DOCUMENTS

| | | |
|---|---|---|
| CN | 102015094 A | 4/2011 |
| CN | 103923355 A | 4/2014 |
| CN | 105431378 A | 3/2016 |
| EP | 1131383 B1 | 10/2003 |
| EP | 1071500 B1 | 3/2005 |
| EP | 2424875 A1 | 3/2012 |
| WO | 2009/126603 A1 | 10/2009 |
| WO | 2015/137860 A1 | 9/2015 |
| WO | 2015/200526 A1 | 12/2015 |

OTHER PUBLICATIONS

Capto Core700: Data File 28-9983-07 AA—Multimodal Chromatography; GE Healthcare Life Sciences; (Mar. 2012); pp. 1-4.
Purification of influenza A/H1N1 using Capto Core 700: Application Note 29-003-34; GE Healthcare Life Sciences; (Mar. 2012); pp. 1-8.
BioSepra HA Ultrogel, product note, CIPHERGEN BioSepra Process Division; (Oct. 2002); pp. 1-4.
BioSepra HA Ultrogel, product insert, Insert No. 292200; PALL Life Sciences; (Mar. 2007); 2 pages.
Zhang, Y. et al.; "Light-Induced Crosslinkable Semiconducting Polymer Dots"; *Chem Sci.*; vol. 6, No. 3; (Mar. 2015); pp. 2102-2109.
International Search Report and Written Opinion from Application No. PCT/US2017/053218, dated Jan. 29, 2018.
Extended European Search Report in EP Appln. 17857258.2 dated May 28, 2020; 8 pages.
Rezvani, A. et al.; "Characterization of a Novel Agarose-Nickel Composite Matrix for Protein Nanoparticles Affinity Chromatography in Expanded Bed"; Chromatographia; vol. 77, No. 19-20; Jul. 18, 2014; pp. 1267-1274.
Manfredi, J.J. et al.; "Purification and Characterization of Two Distinct Complexes of Assembly Polypeptides from Calf Brain Coated Vesicles That Differ in Their Polypeptide Composition and Kinase Activities"; The Journal of Biological Chemistry; vol. 262, No. 25; Sep. 5, 1987; pp. 12182-12188.

* cited by examiner

*Primary Examiner* — Yunsoo Kim
(74) *Attorney, Agent, or Firm* — Kilpatrick Townsend and Stockton LLP

(57) ABSTRACT

Methods and kits for purifying protein-nanoparticle conjugates are provided. In some embodiments, a multimodal medium having a size exclusion mode and a capture mode is used to purify the protein-nanoparticle conjugates.

9 Claims, No Drawings

US 11,905,335 B2

PROTEIN-NANOPARTICLE CONJUGATE PURIFICATION METHODS

This application is a continuation of U.S. patent application Ser. No. 15/714,736, filed Sep. 25, 2017, which is now U.S. Pat. No. 10,934,366, issued Mar. 2, 2021, which claims the benefit of U.S. Provisional Application 62/401,573 filed on Sep. 29, 2016 which is hereby incorporated by reference in its entirety.

BACKGROUND

Nanoparticles (e.g., polymer dots and quantum dots as described in US Patent Application. No. 2012/0282632) are useful reporters when conjugated to proteins. Conjugation reactions between proteins and nanoparticles are generally carried out using a molar excess of protein in order to assure an optimal conjugation ratio. Following conjugation, the conjugate needs to be separated from remaining free protein, since unconjugated protein can interfere with, for example, an assay in which the conjugate is used. Size exclusion chromatography (SEC) and centrifugation have been used to separate the conjugate from excess free protein. SEC requires large columns packed with expensive size exclusion resin. Centrifugation can only be applied to nanoparticles that are relatively dense compared to the medium in which the nanoparticles are suspended. Upon centrifugation, nanoparticle conjugates can also form a pellet that may not be readily dispersible.

SUMMARY

Methods of purifying a protein-nanoparticle conjugate are provided. In some embodiments, the method comprises contacting a mixture of the protein-nanoparticle conjugate, free protein, and a buffer to a multimodal medium to separate the protein-nanoparticle conjugate from free protein, wherein the multimodal medium has a size exclusion mode and a capture mode; and collecting the protein-nanoparticle conjugate from the medium, thereby purifying the protein-nanoparticle conjugate.

In some embodiments, the multimodal medium comprises a polysaccharide and has hydroxyapatite microcrystals entrapped therein. In some embodiments, the multimodal medium comprises a polysaccharide and has a core functionalized with ligands that are both hydrophobic and positively charged. In certain embodiments, one or more of the ligands is octylamine. In some embodiments, the medium further comprises a polysaccharide-based outer shell. In certain embodiments, the polysaccharide is agarose. In some embodiments, the outer shell comprises agarose.

In some embodiments, the multimodal medium comprises acrylamide.

In some embodiments, the nanoparticle is a polymer dot (p-dot). In some embodiments, the p-dot is 5-100 nm in diameter and is a colloidal semiconducting polymer. In some embodiments, the p-dot is fluorescent.

In some embodiments, the mixture further comprises free nanoparticles and the medium separates the free nanoparticles from the conjugate.

In certain embodiments, the mixture comprises a surfactant. In some embodiments, the surfactant is Pluronic F68 and/or polyalkylene glycol. In some embodiments, the surfactant in the mixture is at a concentration of 0.02%-1.0%.

In certain embodiments, the protein is an antibody. In some embodiments, the antibody is an IgG antibody.

In some embodiments, the collecting step comprises collecting one or more fractions enriched for the protein-nanoparticle conjugate from the medium. In certain embodiments, the collecting step comprises applying centrifugal force or a vacuum to the medium and collecting one or more fractions enriched for the protein-nanoparticle conjugate from the medium.

In an embodiment, a kit for purifying a protein-nanoparticle conjugate from free protein comprises a column (e.g., a spin column) and a multimodal medium having a size exclusion mode and a capture mode. In some embodiments, the kit further comprises at least one component consisting of nanoparticles, a buffer, a surfactant, a conjugating agent, and instructions for performing a method of purifying a protein-nanoparticle conjugate from free protein. In some embodiments, the multimodal medium comprises a polysaccharide and has hydroxyapatite microcrystals entrapped therein. In some embodiments, the multimodal medium comprises a polysaccharide and has a core functionalized with ligands that are both hydrophobic and positively charged. In some embodiments, one or more of the ligands is octylamine. In some embodiments, the kit further comprises at least one component consisting of nanoparticles, a buffer, a surfactant, a conjugating agent, and instructions for performing a method of purifying a protein-nanoparticle conjugate from free protein. In some embodiments, the nanoparticles are polymer dots. In some embodiments, each of the polymer dots is 5-100 nm in diameter and is a colloidal semiconducting polymer. In some embodiments, the polymer dot is fluorescent. In some embodiments, the surfactant is Pluronic F-68. In some embodiments, the column is a spin column.

DETAILED DESCRIPTION

The inventors have discovered a novel combination of chromatography medium and conditions that allow for separation of protein-nanoparticle conjugates (e.g., antibody-polymer dot conjugates) from free protein (e.g., free antibody).

I. Definitions

The term "antibody" refers to an immunoglobulin or fragmentary form thereof. The term includes, but is not limited to, polyclonal or monoclonal antibodies of the classes IgA, IgD, IgE, IgG, and IgM, derived from human or other mammalian cell lines, including natural or genetically modified forms such as humanized, human, single-chain, chimeric, synthetic, recombinant, hybrid, mutated, grafted, and in vitro generated antibodies. "Antibody" encompasses composite forms including, but not limited to, fusion proteins containing an immunoglobulin moiety. "Antibody" also includes antibody fragments such as Fab, F(ab')2, Fv, scFv, Fd, dAb, Fc and other compositions, whether or not they retain antigen-binding function.

The term "protein" is used to denote an amino acid polymer or a set of two or more interacting or bound amino acid polymers. The term applies to amino acid polymers in which one or more amino acid residue is an artificial chemical mimetic of a corresponding naturally occurring amino acid, as well as to naturally occurring amino acid polymers, those containing modified residues, and non-naturally occurring amino acid polymers.

II. Methods

A method of purifying a protein-nanoparticle conjugate will now be described. In an embodiment, the method comprises contacting a mixture of the protein-nanoparticle conjugate, free protein, and a buffer to a multimodal medium to separate the conjugate from free protein and optionally from free nanoparticles.

It is believed that the purification method described herein can be applied to a wide range of protein-nanoparticle conjugates. In some embodiments, the protein is an antibody. For example, in some embodiments, the antibody is an IgA, IgD, IgE, IgG, and IgM antibody. In some embodiments, the antibody is an antigen-binding antibody fragment such as, for example, a Fab, F(ab')2, or Fv, or a fusion protein comprising such fragments. In some embodiments, the antibody is a single-chain antibody, e.g., a scFv, a fusion of the variable regions of the heavy (VH) and light chains (VL) of one or more antibodies. The antibody can be recombinant or naturally-occurring. The antibody can be human, mouse, rat, rabbit, bovine, goat, camel, llama or from other antibody-producing species.

Nanoparticles are particles sized on a nanoscale, e.g., from about 1 nm to about 1000 nm. In some embodiments, the particles are between 1-300 nm, 5-500 nm, or 10-50 nm. Many nanoparticles are roughly spherical in shape, which results in a dimension being the radius or diameter of the spherical particle. The hydrodynamic radius or diameter can also be used to define the nanoparticle size.

In some embodiments, the nanoparticle is a fluorescent semiconducting polymer dot (pdot). Examples of such pdots are described in, e.g., Wu, C., et al., *Chem. Mater.* 21:3816-3822 (2009); Rahim, N. A. A., et al., *Adv. Mater.* 21:3492-3496 (2009), Rong et al., *ACS Nano* 7(1):376-84 (2013); patent publications US 2013/0266957; WO 2012/054525; and US 2012/0282632. Chromophoric pdots can be generated by collapsing polymer into a stable sub-micron sized particle. The pdot nanoparticles provided herein may be formed by any method known in the art for collapsing polymers, including without limitation, methods relying on precipitation, methods relying on the formation of emulsions (e.g. mini or micro emulsion), and methods relying on condensation. The pdot nanoparticle size is dependent on the molecular weight of the polymer used to generate the pdots (see, for example, Zhang, Y., et al., *Chem Sci.* 6(3):2102-2109 (2015) and U.S. Pat. No. 9,382,473). In some embodiments, the molecular weight of each pdot ranges from about 500,000 Daltons to about 15,000,000 Daltons, or from about 1,800,000 Daltons to about 7,000,000 Daltons.

Other exemplary nanoparticles that can be used in methods described herein include, but are not limited to, magnetic nanoparticles, quantum dots, and gold nanoparticles. Magnetic nanoparticles are a class of nanoparticle that can be manipulated using magnetic field gradients. Magnetic nanoparticles are formed from magnetic or paramagnetic elements including, but not limited to, iron, nickel and cobalt and their chemical compounds. Quantum dots are nanoparticles formed from inorganic semiconducting material. Gold nanoparticles (e.g., colloidal gold) have optical properties that are conducive to biomedical applications and are described in, for example, Huang, X., et al., *Journal of Advanced Research* 1(1):13-28 (2010).

Nanoparticles can be functionalized as desired to link the nanoparticle to a protein. Exemplary functionalization of nanoparticles is described in the aforementioned US Patent Publication No. 2012/0282632. As an example, a nanoparticle can be functionalized to present one or more carboxylic acid moieties, which in turn can be used via one or more linker to a protein. The conjugate components (e.g., protein and nanoparticle) can be linked covalently or non-covalently. An example of a non-covalent linkage is a biotin-streptavidin affinity linkage in which one member of the conjugate is biotinylated and the other member of the conjugate is linked to streptavidin. Other examples of linkage options include, but are not limited to, direct coupling of nanoparticles to protein amines; modification of nanoparticles with maleimide and subsequent linkage to an protein having an exposed thiol group (generated, for example, by treating the protein with mercaptoethylamine or 2-iminothiolane (Traut's reagent)); modification of nanoparticles with hydrazine and linkage to a protein with oxidized glycan (aldehyde); or use of click chemistry (e.g., modification of nanoparticles with strained alkyne and linkage to an protein modified with azide).

Any type of conjugation methods can be used for conjugating an protein to a nanoparticle. Generally, to generate a desired yield of conjugate, an excess of protein is provided in the conjugation reaction. This can result in a significant amount of free (unconjugated) protein following the conjugation reaction. In some embodiments, there is also an amount of free unconjugated nanoparticles in the reaction mixture. The methods described herein are useful for purifying the conjugates from the free unconjugated members of the conjugation reaction. In some embodiments, a reagent is applied that will react with remaining reactive groups and prevent further reaction. As an example, conjugation between a maleimide-functionalized nanoparticle and a thiolated or reduced protein will be stopped or quenched with an alkylating reagent including, but not limited to, N-ethylmaleimide. The reaction between an NETS-appended nanoparticle and a protein will be stopped or quenched with an amine including, but not limited to, ethanolamine.

Once a conjugation has been performed, the resulting conjugation mixture (e.g., nanoparticle/protein conjugate, unreacted free protein, and optionally free nanoparticle) is adjusted to establish an appropriate pH, conductivity, and/or concentration of salts. Adjustments can be made to the conjugation mixture by, for example, exchanging a conjugation buffer with a chromatography resin equilibration buffer. Exemplary buffering compounds include, but are not limited to, phosphate, HEPES, IVIES, and Tris. In some embodiments, the equilibration buffer comprises HEPES in an amount ranging from about 10 mM to about 30 mM (e.g., 10 mM, 20 mM or 30 mM). In some embodiments, the equilibration buffer comprises phosphate ($PO_4^{3-}$) in an amount ranging from about 5 mM to about 50 mM (e.g., 5 mM, 10 mM, 25 mM). In certain embodiments, the equilibration buffer pH ranges from about 5 to about 8 (e.g., about 6, about 7, or about 8). In some embodiments, the equilibration buffer comprises at least 10 or 100 mM $Na^+$ or $K^+$ (e.g., between 10-150 mM, 20-200 mM, or 100-300 mM). In certain embodiments, the equilibration buffer is 20 mM HEPES-KOH pH 7.3. In some embodiments, the equilibration buffer is phosphate buffered saline (PBS=10 mM sodium phosphate, 150 mM sodium chloride pH 7.8).

One or more surfactants can also be included in the mixture. A sufficient amount of the surfactant can be included to prevent aggregation and precipitation of the conjugates from the mixture, especially upon introduction of a high ionic strength buffer, which might otherwise result in aggregation or precipitation of the conjugates. In some embodiments, the surfactant is a nonionic polyalkylene glycol surfactant such as polyethylene glycol. In some embodiments, the surfactant is a polyoxypropylene-containing surfactant such as a poloxamer surfactant. Poloxamer surfactants are characterized by a central hydrophobic chain of polyoxypropylene (poly(propylene oxide)) flanked by two hydrophilic chains of polyoxyethylene (poly(ethylene oxide)). Because the lengths of the polymer blocks can be customized, many different poloxamers exist that have slightly different properties. Poloxamer copolymers are commonly named with the letter "P" (for poloxamer) followed by three digits, the first two digits×100 give the approximate molecular mass of the polyoxypropylene core, and the last digit×10 gives the percentage polyoxyethylene content (e.g., P407=Poloxamer with a polyoxypropylene molecular mass of 4,000 g/mol and a 70% polyoxyethylene content). For the Pluronic and Synperonic poloxamer tradenames, coding of these copolymers starts with a letter to define its physical form at room temperature (L=liquid, P=paste, F=flake (solid)) followed by two or three digits. The first digit (two digits in a three-digit number) in the numerical designation, multiplied by 300, indicates the approximate molecular weight of the hydrophobic chain; and the last digit×10 gives the percentage polyoxyethylene content (e.g., F-68 indicates a polyoxypropylene molecular mass of 1,800 g/mol and a 80% polyoxyethylene content). An exemplary poloxamer surfactant includes, but is not limited to, Pluronic F-68. The concentration of the surfactant used can be determined empirically (i.e., titrated such that precipitation of the conjugates does not occur). In some embodiments, the concentration of surfactant is 0.02%-1%, e.g., 0.05-0.2%, e.g., 0.1%.

Prior to contacting the conjugate mixture to the multimodal medium, the medium can be equilibrated to establish an appropriate pH, conductivity, and/or concentration of salts. The multimodal medium has a size exclusion mode and a capture mode. The size exclusion mode separates molecules, complexes or particles based on their size or molecular weight. The medium has pores sized such that molecules, complexes or particles above a characteristic size threshold are excluded from entering the pores and are collected in a void volume, an excluded volume or in a chromatography column flow through. Smaller proteins and other molecules can enter the pores of the medium and are captured by the medium. As used herein, a molecular weight cutoff size of the medium refers to the approximate size of the protein or molecule that is able to enter the pores. For example, a molecular weight cutoff size of 50 kDa means that molecules of approximately 50 kDa or less in size can enter the pores of the medium, whereas molecules of approximately more than 50 kDa will be excluded from the pores.

Based on a ligand within the medium (e.g., within the pores of the medium or within a core of a bead-based medium) or a charged group within the medium, the capture mode captures or binds to molecules retained within the medium. Thus, when the mixture of conjugate and free protein is contacted to the multimodal medium, the large conjugate is excluded from entering the pores of the medium and is collected in the void volume. The free proteins (and, optionally, free nanoparticles) small enough to enter the pores are captured by the ligand within the medium or by the charged groups within the medium.

As used herein, the term ligand refers to an entity that binds to applied protein through one or more binding modes including, but not limited to, electrostatic, hydrophobic, Van der Waals, metal affinity, hydrogen bonding and covalent interactions. Electrostatic interactions are mediated by charged groups that bind to oppositely charged molecules on, for example, proteins or dyes that interact with proteins based on hydrophobic and electrostatic forces. Exemplary positively charged groups include, but are not limited to, amine groups, amide groups or other groups capable of carrying a positive charge. Exemplary negatively charged groups include, but are not limited to, carboxylic acid, hydroxyl, thiol, phosphate, sulfonyl or other groups capable of carrying a negative charge. Hydrophobic interactions are mediated by non-polar groups such as alkyl chains and aromatic groups. Ligands may bind to proteins through multiple binding modes. Examples include dye-binding in which protein may bind to immobilized dye through ionic, hydrophobic and hydrogen bonding interactions. Exemplary dyes are described in, for example, Tamburro, D, et. al., *J. Am. Chem. Soc.*, 133, 19178-19188 (2011) and can include anthracene dyes (e.g., Alizarin Blue Black B, Disperse Blue 3, Acid Black 48), anthraquinone dyes (Remazol Brilliant Blue R, Pigment Red 177), dinitrobenzene dyes (Disperse Yellow 3, Disperse Yellow 9), analine dyes (Disperse Orange 3, Acid Black 1, Acid Blue 22, Pararosaniline Base), Rhodamine 123, Toluidine Blue 0, indocyanine green, Cibacron Blue F3GA, triphenylmethane dyes (e.g., Coomassie® Blue), triarylmethane dyes, and eosin dyes. Another example of a ligand that binds protein through multiple binding modes is hydroxyapatite, which binds protein through ionic and metal affinity interactions (Gorbunoff, M. J. and Timasheff, S. N. *Anal. Biochem.*, 136, 440-445 (1984)).

In an embodiment, the multimodal medium comprises a polysaccharide and has hydroxyapatite microcrystals entrapped therein. In certain embodiments, the polysaccharide has pores that exclude the antibody-nanoparticle conjugate and the hydroxyapatite microcrystals capture the free antibody (and optionally the free nanoparticles). A commercially available example of such a multimodal medium is HA Ultrogel® (available from Pall).

As used herein, "hydroxyapatite" refers to an insoluble hydroxylated mineral of calcium phosphate with the structural formula $Ca_{10}(PO_4)_6(OH)_2$. Its dominant modes of interaction are phosphoryl cation exchange and calcium metal affinity. Hydroxapatite is commercially available in a variety of forms including, but not limited to, ceramic hydroxyapatite which is a chemically pure form of hydroxyapatite that has been sintered at high temperature.

In some embodiments, the multimodal medium comprises a polysaccharide and has a core functionalized with ligands that are both hydrophobic and positively charged. In certain embodiments, the polysaccharide has pores that exclude the antibody-nanoparticle conjugate and the ligands capture the free antibody (and optionally the free nanoparticles). In some embodiments, the ligands are octylamine. In some embodiments, the medium further includes a polysaccharide-based outer shell with pores that exclude the antibody-nanoparticle conjugate. A commercially available example of such a multimodal medium is Capto™ Core 700 (available from GE Healthcare).

In some embodiments, the polysaccharide in the multimodal medium is agarose. In some embodiments, the polysaccharide is dextran.

In certain embodiments, the multimodal medium comprises acrylamide. In some embodiments, the multimodal medium comprises polymers having cross-linkable units and the degree of crosslinking will determine the pore size of the medium. In some embodiments, the multimodal medium comprises polymers formed from n-isopropylacrylamide and has a core functionalized with dye-based affinity ligands. Examples of such a multimodal medium that comprises acrylamide having a core functionalized with dye-based affinity ligands is described in, for example, U.S. Pat. Nos. 8,382,987; and 9,383,299.

The multimodal medium can be used in any conventional purification configuration including, but not limited to, packed columns and fluidized or expanded-bed columns and by any conventional chromatography method including batch modes for loading, washing, and elution, as well as continuous or flow-through modes. In some embodiments, the medium is packed in a column having a diameter ranging from less than 0.5 centimeter to more than a meter and a column height ranging from less than one centimeter to more than 30 centimeters. In an embodiment, the medium is provided in a disposable spin column. The sample is applied to the top of the spin column and centrifugation or vacuum forces the sample through the column. In some cases, the medium is provided in a chromatography column, the sample is applied to the top of the column and gravity forces the sample through the column.

After contacting the protein-nanoparticle conjugate, free protein, and buffer mixture to the multimodal medium, the protein-nanoparticle conjugate is collected from the medium, thereby purifying the protein-nanoparticle conjugate from the free protein and, optionally, the free nanoparticles.

The output from the multimodal medium can be monitored for the presence of the conjugate, free protein, or other components of the sample, as desired, to determine fractions that contain the conjugate and that are free, or at least have a reduced amount, of free antibody compared to the original conjugation mixture. In some embodiments, at least 90%, 95%, 99% of the unconjugated protein in the conjugation reaction is removed in the resulting purified conjugate fractions. An exemplary method for measuring output includes monitoring a characteristic absorbance wavelength for the nanoparticle or protein. The term "fraction" is used to refer to a portion of the output of chromatography and is not intended to limit how the output is collected or whether the output is collected in parts or continuously.

III. Kits

Kits for purifying a protein-nanoparticle conjugate according to methods described herein are provided. In some embodiments, a kit comprises a column (e.g., a spin column) and a multimodal medium having a size exclusion mode and a capture mode. In some embodiments, the multimodal medium comprises a polysaccharide and has hydroxyapatite microcrystals entrapped therein. In certain embodiments, the multimodal medium comprises a polysaccharide and has a core functionalized with ligands that are both hydrophobic and positively charged. In some embodiments, the ligands are octylamine. In some embodiments, the multimodal medium comprises polymers formed from n-isopropylacrylamide and has a core functionalized with dye-based affinity ligands. In certain embodiments, the kit further comprises nanoparticles (e.g., functionalized pdots), a buffer, a surfactant, a conjugating agent for conjugating the protein to the nanoparticle, and/or instructions for purifying a protein-nanoparticle conjugate from free protein.

IV. EXAMPLES

Example 1: Purification of IgG-Polymer Dot Conjugate Using Gravity Columns

This example illustrates the purification of an IgG-polymer dot (pdot) conjugate from free IgG using gravity columns.

Materials:
1. 1.5 mls Capto™ Core 700 resin (GE Healthcare)
2. 3 mls HA Ultrogel® resin (VWR catalog #87004-866)
3. 2 ml disposable gravity columns (Thermo Fisher catalog #29920)
4. 300 µl goat anti-rabbit IgG-pdot conjugation reaction mixture containing unreacted free IgG.
5. Column equilibration and Wash Buffer #1: PBS (150 mM sodium chloride, 10 mM sodium phosphate pH 7.8) and (0.1% Pluronic F68+0.1% PEG 3350 to inhibit nanoparticle aggregation)
6. Wash Buffer #2: 20 mM potassium HEPES pH 7.3, 0.1% Pluronic F68, and 0.1% PEG 3350

Three columns were prepared as follows: 1.5 ml of the Capto™ Core 700 resin was poured into column #1 and 1.5 ml HA Ultrogel® resin was poured into each of columns 2 and 3. The resin in all the columns was allowed to settle. The columns were equilibrated with column equilibration buffer (i.e., Wash Buffer #1) or Wash Buffer #2, depending on the resin (see Table 1). 100 µl of the conjugation reaction mixture was applied to each of the columns. The columns were eluted with Wash Buffer #1 or Wash Buffer #2 depending on the resin (see Table 1). The pdots used in the conjugate have a brownish-red color and have an absorbance at 473 nm (or A473). The volume and A473 (i.e., the absorbance of the pdots) was determined for each column flow through and was used to determine the yield based on the pdots. Free IgG in each column flow through was determined by analyzing a portion of each flow through by non-denaturing SDS-PAGE. Pdots do not enter a polyacrylamide gel; thus, the gel was used to estimate the concentration of free IgG in each column flow through (e.g., by using densitometry to generate a standard curve from which the concentration of free IgG was determined). The estimated concentration of IgG was used to estimate the percent IgG clearance by comparison to the original mass of IgG in the reaction mixture. Referring to Table 1, the percent IgG-pdot conjugate yield and the percent IgG clearance or removal (i.e., 100–percent free IgG) were determined relative to the control (i.e., unfractionated material).

TABLE 1

| Treatment | IgG-pdot Conjugate Yield (%) | IgG Clearance (%) |
| --- | --- | --- |
| Control: unfractionated conjugate | 100 | 0 |
| Column 1: Capto ™ Core 700 washed with Wash Buffer #1 | 35 | 97.3 |
| Column 2: HA Ultrogel ® washed with Wash Buffer #1 | 87 | 90.2 |
| Column 3: HA Ultrogel ® washed with Wash Buffer #2 | 84 | 95.9 |

The results in Table 1 show that the percent conjugate yield with HA Ultrogel® with Wash Buffer #1 is higher than the percent conjugate yield with Capto Core 700. The percent conjugate yield with HA Ultrogel® was 87% and 84%, respectively, for Wash Buffers 1 and 2. The results in Table 1 also show that both types of resin removed or cleared at least 90% of the free antibody.

The example illustrates the use of two different multimodal media having a size exclusion mode and a capture mode (i.e., HA Ultrogel® and Capto™ Core 700) to purify IgG-pdot conjugate from free IgG.

Example 2: Purification of IgG-Polymer Dot Conjugate Using Spin Columns

This example illustrates the purification of an IgG-pdot conjugate from free IgG using spin columns.

Materials:
1. HA Ultrogel® resin (VWR catalog #87004-866)
2. Disposable spin columns (Thermo Fisher catalog #69705)
3. Twenty-three samples: 23 goat anti-rabbit IgG-pdot conjugation reaction mixtures containing free IgG. Each conjugation reaction mixture used a different lot of pdots. The conjugation reaction mixtures contained 120-167 µg pdot and 0.5 times the pdot mass in IgG.
4. Column equilibration buffer: 20 mM potassium HEPES pH 7.3, 0.1% Pluronic F68, and 0.1% PEG 3350

Spin columns were prepared by pipetting 200 µl of HA Ultrogel® slurry (i.e., HA Ultragel resin suspended in column equilibration buffer) into empty spin columns. The spin columns were equilibrated with column equilibration buffer by 3× repeated application of 500 µl of the buffer followed by centrifugation for 1 minute at 1500×g. The spin columns were plugged and each entire conjugation reaction was applied. Following room temperature incubation for 1 hour, the IgG-pdot conjugates were collected by centrifugation for 2 minutes at 1500×g.

The volume and absorbance at 473 nm (i.e., the absorbance of the pdots) were determined for each reaction mixture and was used to determine the IgG-pdot conjugate yield based on pdots. Free IgG in each reaction was determined by the non-denaturing SDS-PAGE as described in Example 1. The estimated concentration of IgG was used to estimate percent IgG clearance by comparison to the original mass of IgG in the reaction mixture. The percent IgG-pdot conjugate yield and the percent IgG clearance for the 23 reaction mixtures are summarized in Table 2.

TABLE 2

| Sample | IgG-pdot Conjugate Yield (%) | IgG Clearance (%) |
|---|---|---|
| 1 | 79 | 99.3 |
| 2 | 56 | 99.2 |
| 3 | 62 | 99.5 |
| 4 | 107 (apparent) | 99.4 |
| 5 | 82 | 99.5 |
| 6 | 60 | 99.6 |
| 7 | 60 | 99.1 |
| 8 | 75 | 99.5 |
| 9 | 74 | 99.5 |
| 10 | 63 | 99.7 |
| 11 | 67 | 99.5 |
| 12 | 48 | 99.1 |
| 13 | 100 | 99.1 |
| 14 | 90 | 99.2 |
| 15 | 50 | 99.1 |
| 16 | 57 | 98.4 |
| 17 | 69 | 98.4 |
| 18 | 74 | 98.5 |
| 19 | 86 | 99.2 |
| 20 | 69 | 99.1 |
| 21 | 79 | 98.4 |
| 22 | 70 | 99.4 |
| 23 | 88 | 99.0 |

The results in Table 2 show that the percent conjugate yield with HA Ultrogel® ranges from 48% to about 107% (apparent). The variability in the percent conjugate yield was dependent on the lot of the pdots used in the conjugation reaction mixture. The results in Table 2 also show that at least 98% of the free antibody was cleared from all the samples, regardless of the pdot lot used in the conjugation reaction mixture.

The example illustrates the use of a multimodal resin (i.e., HA Ultrogel®) having a size exclusion mode and a capture mode to purify IgG-pdot conjugate from free IgG using spin columns.

In the claims appended hereto, the term "a" or "an" is intended to mean "one or more." The term "comprise" and variations thereof such as "comprises" and "comprising," when preceding the recitation of a step or an element, are intended to mean that the addition of further steps or elements is optional and not excluded. All patents, patent applications, and other published reference materials cited in this specification are hereby incorporated herein by reference in their entirety. Any discrepancy between any reference material cited herein or any prior art in general and an explicit teaching of this specification is intended to be resolved in favor of the teaching in this specification. This includes any discrepancy between an art-understood definition of a word or phrase and a definition explicitly provided in this specification of the same word or phrase.

What is claimed is:

1. A kit for purifying a protein-nanoparticle conjugate from free protein, the kit comprising:
   a column;
   a multimodal medium having a size exclusion mode in which pores in the medium exclude the antibody-nanoparticle conjugate and a capture mode in which ligands or charged groups within the medium capture the free protein and the multimodal medium comprises a polysaccharide that is agarose and has hydroxyapatite microcrystals entrapped therein;
   a surfactant; and
   a polyalkylene glycol.

2. The kit of claim 1, wherein the surfactant is a poloxamer surfactant.

3. The kit of claim 2, wherein the polyalkylene glycol is polyethylene glycol.

4. The kit of claim 2, wherein the poloxamer surfactant is a F-68 poloxamer surfactant.

5. The kit of claim 1, wherein the nanoparticle is a polymer dot.

6. The kit of claim 5, wherein the polymer dot is 5-100 nm in diameter and is a colloidal semiconducting polymer.

7. The kit of claim 5, wherein the polymer dot is fluorescent.

8. The kit of claim 1, further comprising a HEPES buffer.

9. The kit of claim 8, wherein the poloxamer surfactant is a F-68 poloxamer surfactant and the polyalkylene glycol is polyethylene glycol.

* * * * *